United States Patent [19]
Deutsch

[11] Patent Number: 5,138,269
[45] Date of Patent: Aug. 11, 1992

[54] METHOD AND MEANS FOR MEASURING THE DEPTH OF CRACKS

[75] Inventor: Volker Deutsch, Wuppertal, Fed. Rep. of Germany

[73] Assignee: Karl Deutsch Prüf - und Messgerätebau GmbH + Co. KG, Wuppertal, Fed. Rep. of Germany

[21] Appl. No.: 396,447

[22] Filed: Aug. 18, 1989

[30] Foreign Application Priority Data

Aug. 23, 1988 [DE] Fed. Rep. of Germany ....... 3828552

[51] Int. Cl.$^5$ .............................................. G01R 27/24
[52] U.S. Cl. ................................. 324/715; 324/718; 324/713
[58] Field of Search ............... 324/64, 65 R, 713, 715, 324/717, 718

[56] References Cited

U.S. PATENT DOCUMENTS

| | | | |
|---|---|---|---|
| 3,735,254 | 5/1973 | Severin | 324/64 |
| 4,178,543 | 12/1979 | Wrinn et al. | 324/718 |
| 4,656,545 | 4/1987 | Hognestad | 324/718 |
| 4,667,149 | 5/1987 | Cohen et al. | 324/64 |
| 4,706,015 | 11/1987 | Chen | 324/64 |
| 4,764,970 | 8/1988 | Hayashi et al. | 324/715 |

FOREIGN PATENT DOCUMENTS

| | | | |
|---|---|---|---|
| 159274 | 8/1980 | Fed. Rep. of Germany | 324/64 |
| 2012965 | 8/1979 | United Kingdom | |
| 2161936 | 1/1986 | United Kingdom | |

OTHER PUBLICATIONS

Matting & Deutsch, "ie Möglichkeiten genaur Risstiefenmessungen", Sonderdruck Aus Materialprüfung Band Mar./1961 NR 6, S.

Primary Examiner—Kenneth A. Wieder
Assistant Examiner—Maura K. Regan
Attorney, Agent, or Firm—Akoo-Toren

[57] ABSTRACT

The invention relates to a method and means for measuring the depth of cracks, using a potential probe connected to a measuring instrument and having two current terminals and additional voltage-measuring terminals (potential probe method).

The object of the invention is to eliminate the separate calibration devices needed for the checks and collective measurements necessary when using known potential probes, and to make the check measurements in conjunction with the actual depth-measuring process.

This problem is solvable by using a potential probe (S) as per the drawing, where at least two pairs of terminals (1+2, 3+4) having known but different spacings serve as adjustment measuring portions and are connected to an adjustment circuit (JM, UM) in a measuring-instrument microcomputer (M) and an additional pair of terminals (2, 3) having a known spacing serve as a crack-depth measuring portion and are connected to a crack-depth measuring circuit (TM) in the microcomputer. The probe is attached to the workpiece so that the adjustment portions lie on opposite sides of the crack, whereas the crack-depth measuring portion contains the crack.

3 Claims, 1 Drawing Sheet

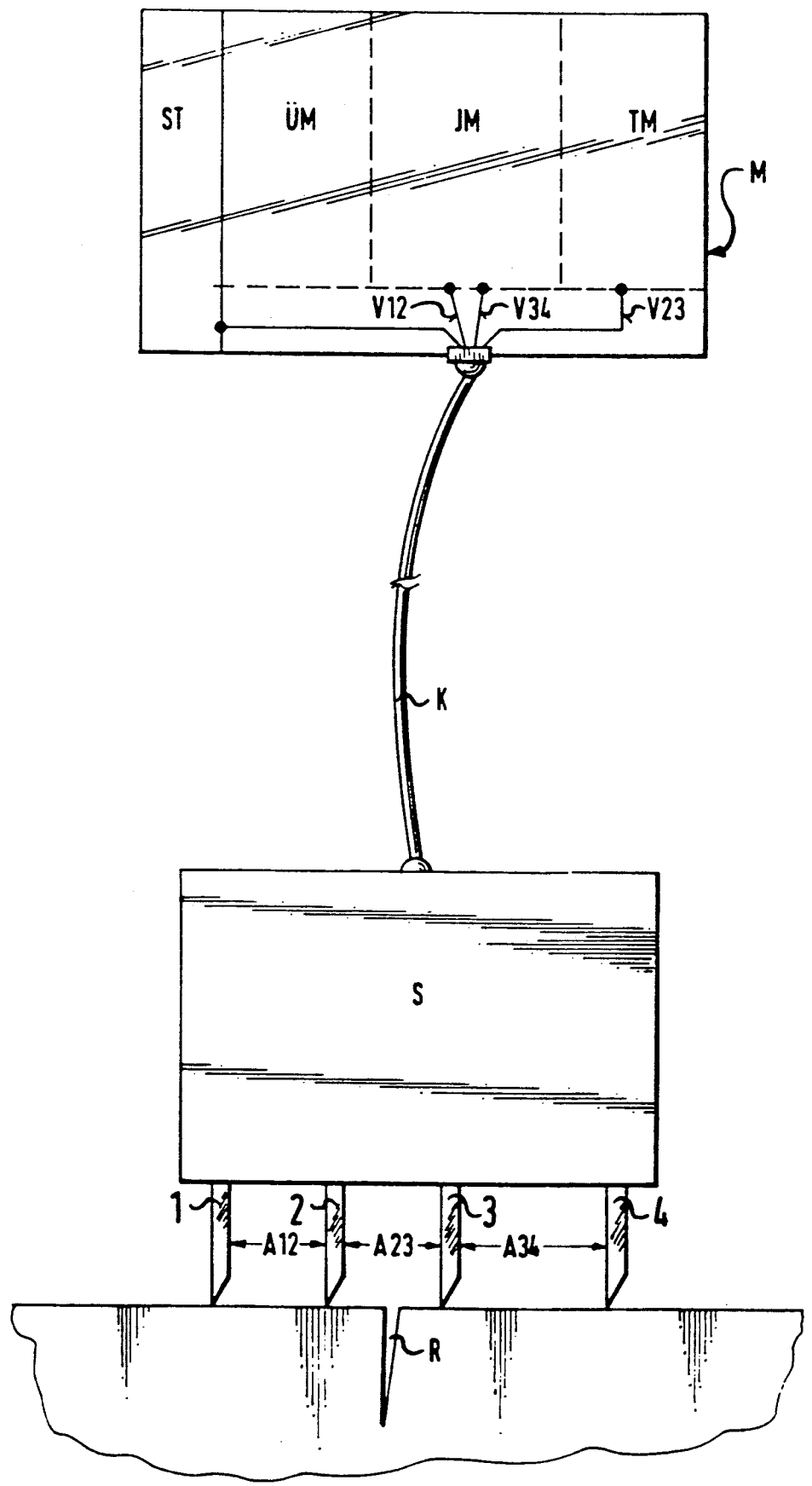

METHOD AND MEANS FOR MEASURING THE DEPTH OF CRACKS

The invention relates to a method of measuring the depth of cracks using a potential probe, in which an electric current, preferably a.c., is sent through the test-piece via two probe current terminals attached to the test-piece on opposite sides of the crack, and two probe measuring terminals disposed on the test-piece at a known spacing from one another on opposite sides of the crack and on the line joining the current terminals measure the voltage drop in the path of the current between the measuring terminals and use it as a criterion to evaluate the depth of the crack by relating it to the voltage drop measured by the probe-current terminals and measuring terminals on a fault-free region of a test-piece having material properties and geometry which are evaluated as equivalent, the last-mentioned voltage drop being used to derive a material correction coefficient included in the evaluation.

The invention also relates to means for working an aforementioned method, comprising a measuring instrument having a source for delivering stabilized current for flowing through the test-piece and an evaluation unit supplied with voltage-drop measurements and converting them into crack-depth values which are supplied to a display unit, and at least one probe connected to the measuring instrument by a flexible cable and having two current terminals (probe tips) supplied by the current source of the instrument and also having voltage-measuring terminals (probe tips) disposed with a fixed known spacing from one another and from the current terminals in the line joining the current terminals, and making measurements which are supplied to the evaluating unit in the measuring instrument.

The main sector of application of the invention is the checking of cracked workpieces to see whether they can be made crack-free by reworking, so that they need not be rejected. The more valuable the workpieces, the more preference will be given to the method of reworking, in an attempt to remove the crack by grinding or other subsequent mechanical treatment. If however the remaining machining allowance is worked off and it is then found that the crack has still not been completely removed, the cost of reworking will have been wasted. This accounts for the economic importance of measuring the depth of crack. In addition, if the depth of a crack is known in time it may be possible, by a suitable method of reworking, to use even those parts which would have been rejected if reworked in normal manner.

Admittedly, the depth of cracks can be measured by the ultrasonic test method or the eddy-current method, but these methods are not as universally applicable as the potential probe method, which has already been used as a supplement for decades, though applicable only to metal workpieces.

The potential probe method is based on the fact that if a current is made to flow into a workpiece between two terminals and if a surface crack lies in its path from one terminal to the other, the current flows round the crack and therefore has to travel a greater distance than if there is no crack in its path between the terminals. The increased travel of the current results in an increase in the potential drop between the two measuring terminals. This increase in the measured potential drop due to a crack in the path of the current can be used to measure the depth of the crack. However, the potential probe method is applicable only if the crack does not extend parallel to the path of the current.

In order however to determine the depth of cracks correctly by the potential probe method, corrections are needed to account for the properties and geometry of the test-piece material and/or unavoidable fluctuations in contact resistance at the probe places constituting the terminals. The influence of these factors is different for d.c. and a.c. When d.c. is used, the most noticeable influences are geometric, whereas a.c. measurements are more influenced by changes in the permeability and conductivity of the material under test.

In order to compensate distortions in measurements due to changes in the properties and geometry of the material and/or fluctuations in the contact resistance at the probe tips, it is known to make corrective and check measurements, inter alia before actually measuring the crack. For the purpose of simplifying these corrective and check measurements, special calibration probes have become known in conjunction with calibration rods. The calibration rods are made of material of known properties and geometry and are formed with a crack of known depth. The calibration probes have four terminals disposed at a uniform known spacing and in the form of probe tips, the two outer terminals being current terminals and the two inner terminals being measuring terminals. Adjustment is made in four steps:

1) The calibration probe is placed on a fault-free part of the calibration rod and a zero-point potentiometer belonging to the measurement instrument is used to adjust the zero point on the indicator of the instrument,
2) The measuring terminals of the calibration probe are attached to opposite sides of the calibration rod and a sensitivity potentiometer on the measuring instrument is used to set the known crack depth on the instrument indicator,
3) The calibration probe is attached to a crack-free part of the calibration rod and the known spacing PA between the measuring terminals is set on the indicator, using the zero-point potentiometer, and
4) In the next step in setting the instrument, the calibration probe is placed on a fault-free part of the test piece, which has unknown material properties and where the depth of a crack is to be measured. The resulting value A displayed for the terminal spacing can be used to calculate the material correction K, i.e. $K = PA/A$.

All measurements subsequently made on the test-piece must be multiplied by this material correction coefficient.

If, owing to the existing surface structure, it cannot be assumed that the contact resistance will always remain the same after repeated attachment, all the aforementioned check and corrective measurements must be made repeatedly.

The object of the invention is to enable the necessary check and corrective measurements to be made without separate calibration devices and in conjunction with the actual depth-measuring process, so that the measurement is quicker and above all is more reliable.

According to the invention, this problem is solved by the features in claim 1 (for the method) and 5 (for the means).

Other features of the invention are disclosed in the sub-claims.

The method according to the invention and an embodiment of a means for working it, given by way of example, are explained in the accompanying description with reference to the drawing. The drawing is a diagrammatic side view of a means according to the invention comprising a measuring probe and—on a considerably smaller scale—a block circuit diagram of an associated measuring instrument.

A measuring probe S comprises four probe tips 1, 2, 3, 4, at least three of which are resilient (resiliently mounted). The probe tips 1, 2, 3, 4 are all designed and connected as measuring probes for the measurement of voltage potentials, but terminals 1 and 4 can additionally be designed as current terminals for supplying a current for flowing through a test-piece P. Alternatively current can be supplied through two separate attachment contacts (not shown) as known for measuring the depth of cracks by the potential probe method, and attached to the test-piece to left and right of the probe, subject to rules known to the skilled addressee. Test-piece P has a crack R, the depth of which is to be measured. The spacing A12 and A23 between the test terminals 1, 2, 3 formed by probe tips 1, 2 and 3 is the same, whereas the terminal spacing A34 between the probe tips 3 and 4 is greater by an amount D, i.e. A34 = A12 + D = A23 + D.

Probe S is connected by a flexible cable K, whose cores are connected to or (partly) comprise the leads to the probe tips 1, 2, 3, 4, to the circuits corresponding in function to the measuring terminals 1, 2, 3, 4 in a measuring instrument M containing a microcomputer in which the measurements from terminals 1, 2, 3, 4 can be compared with one another according to the invention and linked to measurment parameters fed to the computer, as will be explained hereinafter.

The terminal pairs 1+2 amd 3+4 constitute two adjustment measuring portions having different terminal spacings A12 and A34 = A12 + D, which are or can be input to the computer in the evaluating unit of the measuring instrument. The terminals pairs 1+2 and 2+3 are connected to an adjustment measuring circuit JM in the evaluating unit AE of the measuring instrument, for determining a material correction coefficient K. To this end the adjustment circuit JM is equipped with a comparator for comparing the two voltage measurements V12 and V34 supplied from the adjustment portions of the probe S and determining the resulting comparative value $\Delta$ V12, 34, which is supplied to a logic circuit. A store in the adjustment circuit JM is for storing the terminal-spacing differential value D for the probe used for the measurement; this value can be called into the logic circuit, in which it is associated with the voltage comparison value $\Delta$ V12, 34 in order to obtain the material correction coefficient K, e.g. by means of the relation $(1 + D/A12)$ or $(1 - D/A34)$ in connection with the comparative value $\Delta$ V12, 34.

The terminal pair 2+3, whose spacing A23 is equal to the spacing of one adjustment terminal pair 1+2, i.e. equal to A12, constitutes the portion for measuring the depth of a crack, which is or can be connected to a crack-depth measuring circuit TM in the evaluation unit AE of the measuring instrument. In circuit TM the voltage measurement V23 supplied from the measuring portion between terminals 2 and 3 is compared with the measured value V12 or V34 from one of the adjustment portions 1+2 or 3+4 to obtain the comparative value $\Delta$ V12, 23 or $\Delta$ V23, 34, which is proportional to the depth of the crack and can be used in conjunction with the material corrective coefficient V to obtain the depth of crack, the value of which can be displayed on a display device (not shown).

In order to make corrections to allow for changes in the contact resistance at the terminals, the measuring unit is equipped with a terminal-contact monitoring and corrective circuit UM. The circuit compares the material correction coefficient K obtained in the adjustment circuit with limiting values G stored in a store for the plausibility range of the corrective value, which is obtained from the spacing difference D and the measured voltage values V12, V34 in relation to the spacings A12, A34. If the measured value K does not lie inside the plausibility range, the circuit UM gives a blocking signal for the depth measurement, which indicates that the contact resistances at the terminals have deviated impermissibly from one another during the adjustment measurement and consequently the result will be incorrect if the measured corrective coefficient K is used to determine the depth.

The monitoring and corrective circuit UM can also be equipped for storage of limiting values for the tolerance limits of the measured corrective values, and can comprise a comparator by means of which corrective coefficients K obtained after successive attachment of the probe and lying within the plausibility range are compared with the tolerance limits, which set a minimum accuracy of measurement.

A current generator ST in the measuring instrument delivers a stabilized current for flowing through the test-piece and supplied through cable K to the current terminals, which are not shown or marked as such in the drawing. The current terminals can either be separate or alternatively the contact tips 1 and 4 can additionally be equipped as current terminals.

On the basis of experience with conventional crack-depth measuring instruments, a medium-frequency a.c., e.g. of frequency 1.5 kHz, is normally made available in the current generator ST for flowing through the test-piece. This frequency can be used to measure the slope of a crack by comparing the measured voltage drops V12 and V34 in the crack-free adjustment measurement portions 1+2 and 3+4 in the case where there is a crack in the measured portion 2+3 and in the case where the portion between the terminal pair 2+3 is free from cracks. It is important to determine the slope of the crack, because in the case of sloping cracks it is desirable to determine, not the actual length of the crack but the projection thereof in a plane perpendicular to the surface of the crack, because this determines the extent to which the workpiece has to be machined to obtain a crack-free surface. In this connection the term "crack length" means the extent of the crack from the surface in the depth direction in the plane of the crack, which is at an angle to the surface. When d.c. or low-frequency a.c. is used for the through current when measuring the depth of cracks, the projection of the crack length perpendicular to the surface is displayed, whereas in the case of high-frequency a.c. the crack length is measured as a result of the progressively increasing skin effect. Advantageously the frequency of the flow-through current is adjustable.

Using the previously-described means, the depth of cracks is measured by the following method:

If a sloping crack can be excluded, as experience shows is the case with fatigue cracks, the probe S is attached to the workpiece so that the crack, the depth of which is to be measured, lies between terminals 2 and 3. The voltage drops V12 and V34 occurring between terminals 1, 2, 3, 4 when the probe is in the aforementioned position and a current flows through, are used as adjustment measured values and supplied to the adjustment circuit JM and, by means of the comparison value obtained by comparison thereof and the terminalspacing differential value D stored in the computer, the computer in the adjustment circuit JM of the evaluating unit AE of the measuring instrument M determines the corrective coefficient K and, by comparison with the limiting values G in the circuit UM, checks whether the coefficient lies in the plausibility range. If this is not the case, this indicates differences in contact resistances at the terminals. A blocking signal is triggered and indicates this fact to the operator. Subsequent evaluation must be delayed until plausible conditions are obtained after repeated attachment, if required after improving the surface of the test-piece by additional machining in the contact region. The conditions are improved if, after the probes have been repeatedly attached in the case of a crack in portion 2, 3, the differential values fluctuate not only within the plausibility range but also only within the tolerance likewise stored in the computer. If it has been shown in this manner that the surface of the test-piece has been prepared for measurement and the measurements for determining the coefficient K have been performed with uniform contact resistances at the terminals, the actual crack depth can be measured in the same operation, by comparing the voltage drop V23 in portion 2+3 in the crack-depth measuring circuit TM with one of the two voltages V12 and V34 for the crack-free portions and using the resulting comparative value V12, 23 or V23, 34 in conjunction with the correction coefficient K in the computer to determine the depth of the crack and display it in the display device.

If a sloping crack cannot be excluded, which is usually the case only when the crack is not due to fatigue but has been produced during the process of manufacturing the test-piece, e.g. during casting, it is advantageous initially to make the adjustment measurements on a part of the workpiece surface which is fault-free also in the probe portion 2+3, i.e. the probe is initially attached in such a manner that there is no crack between terminals 2 and 3. When the probe is in this position, the previously-mentioned measuring steps are carried out in portions 1+2, 3+4 and 2+3, so as to determine the correction coefficient K and the "zero" depth of crack. The probe is then attached so that the crack to be measured is between terminals 2 and 3, and the corrective coefficient K is again determined by measuring the voltage comparative value Δ V12, 34 and its relation to the terminal-spacing differential value D, using the computer as before. If the coefficient K agrees with the value K measured in the fault-free part of the surface, the conditions are right for efficient measurement of the depth of the crack, i.e. the crack extends perpendicular to the surface and the contact resistances are the same. The depth can then be measured by evaluating the measured voltage V23 by comparison with the voltage measured for one of the adjustment portions 1+2 or 3+4 and by relating the resulting comparative value to the correction coefficient K.

If however the adjustment measurements on the fault-free part of the workpiece surface yield different correction coefficients K from the measurements in the fault region, the blocking signal is triggered and prevents the depth being measured. If the deviation between the correction coefficient for the crack region and the coefficient obtained by measurement on the crack-free part of the surface cannot be eliminated by reworking the surface of the workpiece in the cracked region, the crack will be sloping. In that case the differences between the measured correction coefficients can be deliberately evaluated to obtain the crest of the sloping position of the crack. The resulting value depends on the test frequency. In this case therefore it may be advantageous to make successive measurements with a.c. of varying frequency.

I claim:

1. An apparatus for measuring the depth of cracks, comprising:

a measuring instrument having a source for delivering stabilized current for flowing through the test-piece and evaluation means for converting voltage measurement values supplied to them into crack-depth values which are supplied to a display unit;

at least one measuring probe connected to the measuring instrument by a flexible cable and having two current terminals (probe tips) supplied by the current source of the measuring instrument and also having voltage measuring terminals (probe tips) disposed with a fixed known spacing from one another and from the current terminals in the line joining the current terminals, the voltage values at the measuring terminals being supplied to the evaluating means in the measuring instrument;

the measuring probe comprising at least four measuring terminals (1, 2, 3, 4) out of which at least three neighboring terminals are disposed at a preferably uniform, known spacing (A12, A23) from one another, whereas another terminal (4) has a spacing (A34) from an adjacent terminal (3) which differs from the previously-mentioned spacing by a known amount (D) and is preferably larger, and at least two pairs of terminals (1+2, 3+4) having different terminal spacings are as adjustment measuring portions connectable to an adjustment circuit in the measuring instrument for determining the material correction coefficient, and an additional pair of terminals (2+3) are as a crack-depth measuring portion connectable to a crack-depth measuring circuit in the measuring instrument; and the measuring instrument, which is equipped with a microcomputer, includes the following circuits:

the adjustment circuit comprising a comparator for comparing the values measured by the adjustment measuring portions (12, 34) and a logic circuit for determining a material correction coefficient from the comparative value resulting from this comparison and its associated terminal-spacing difference (D) fed to the computer;

a terminal contact monitoring or correcting circuit comprising a comparator for comparing the measured material correction coefficient with limiting values for the correction coefficient plausibility range storable in the computer and generating a signal for blocking the depth measurement if the limiting values are exceeded, and the crack-depth measuring circuit comprising a comparator for comparing the values measured by the crack-depth measuring portion (23) with the measurements from at least one of the adjustment measuring portions (12, 13) and for determining the comparative value resulting from this comparison, and a logic circuit for determining the crack depth from this comparative value and the measured material correction coefficient.

2. An apparatus according to claim 1, wherein the terminal contact monitoring or correction circuit comprises a comparator for comparing the measured material correction coefficients with limiting values of the tolerance range storable in the computer.

3. An apparatus according to claim 1, wherein the source for generating the flow-through current is adjustable in frequency.

* * * * *